United States Patent
Hayakawa

(10) Patent No.: US 6,616,601 B2
(45) Date of Patent: Sep. 9, 2003

(54) FLEXIBLE TUBE FOR ENDOSCOPE

(75) Inventor: Shinji Hayakawa, Saitama (JP)

(73) Assignee: Pentax Corporation, Tokyo (JP)

( * ) Notice: Subject to any disclaimer, the term of this patent is extended or adjusted under 35 U.S.C. 154(b) by 0 days.

(21) Appl. No.: 09/765,395

(22) Filed: Jan. 22, 2001

(65) Prior Publication Data

US 2001/0029317 A1 Oct. 11, 2001

(30) Foreign Application Priority Data

Jan. 21, 2000 (JP) .......................................... 2000-013105

(51) Int. Cl.$^7$ ................................................. A61B 1/00
(52) U.S. Cl. ........................................ 600/140; 424/726
(58) Field of Search .............................. 600/140, 139, 600/101; 424/726, 725

(56) References Cited

U.S. PATENT DOCUMENTS

| | | | |
|---|---|---|---|
| 4,675,347 A | * 6/1987 | Mochizuki et al. | 106/15.05 |
| 5,165,952 A | * 11/1992 | Solomon et al. | 424/78.08 |
| 5,514,074 A | * 5/1996 | Yabe et al. | 600/121 |
| 5,741,138 A | 4/1998 | Rice et al. | |

FOREIGN PATENT DOCUMENTS

| | | |
|---|---|---|
| JP | 5-220102 | 8/1993 |
| JP | 7-155281 | 6/1995 |
| JP | 7-324038 | 12/1995 |
| JP | 10245312 | 9/1998 |

* cited by examiner

*Primary Examiner*—Thor Campbell
(74) *Attorney, Agent, or Firm*—Greenblum & Bernstein, P.L.C.

(57) ABSTRACT

A flexible tube for an endoscope comprises a flexible elongated structural body and an outer cover provided over the elongated structural body. In this flexible tube, at least the outer peripheral part of the outer cover is made of a material which contains elastic resin and plant extract having an antibacterial property, and the plant extract is prepared using at least one plant selected from the group consisting of plants belonging to the order Ranunculales. Further, in the flexible tube, the plant extract and the resin that constitutes the outer cover are inert with respect to each other. According to the flexible tube described above, it is possible to provide a flexible tube for an endoscope that can not only exhibit excellent antibacterial property against bacteria and the like, but also sustain the antibacterial property over a long period of time.

8 Claims, 3 Drawing Sheets

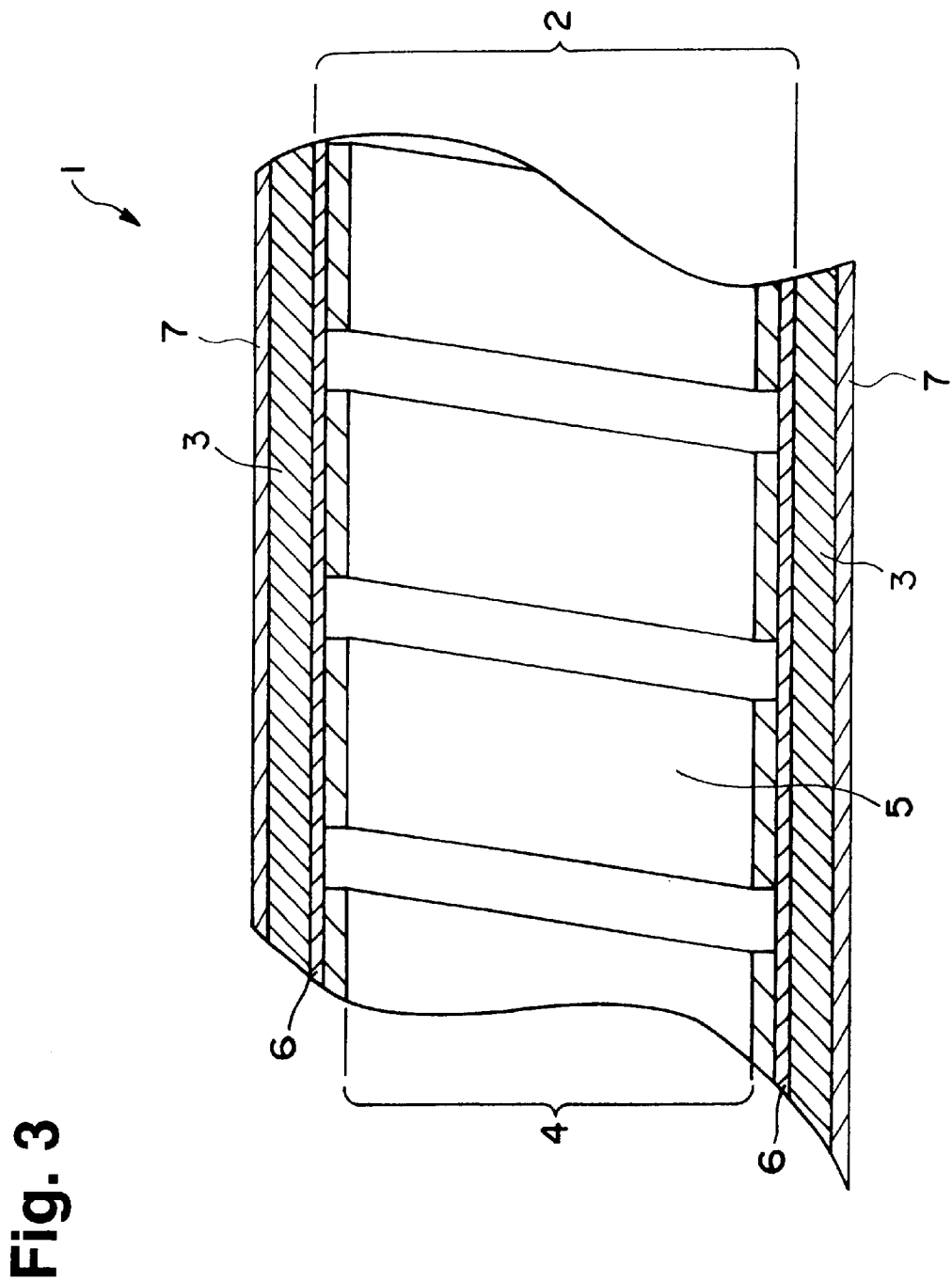

FLEXIBLE TUBE FOR ENDOSCOPE

BACKGROUND OF THE INVENTION

1. Field of the invention

The present invention relates to a flexible tube for an endoscope, which is used by, for example, being inserted into a living body.

2. Description of the Prior Art

In endoscopic examination, a flexible tube of an insertion section of an endoscope (that is, a section of an endoscope to be inserted into a body cavity) is inserted deep into a body cavity, such as stomach, duodenum, small intestine or large intestine.

When the endoscope is inserted into a body cavity, a surface of the flexible tube of the endoscope comes to contact with bacteria (e.g., coli bacteria) resident in the body cavity, so that bacteria adhere on the surface of the flexible tube.

In order to make it possible to use the endoscope repeatedly for many patients, the bacteria adheared onto the flexible tube must be removed. Therefore, the endoscope after use is normally subjected to a high temperature sterilization treatment or a disinfection treatment (that uses a peroxide disinfectant solution).

However, in the medical site, there is a demand that a further countermeasure against bacteria, virus and the like should be taken in order to repeatedly use the endoscope more safely for many patients.

SUMMARY OF THE INVENTION

In view of the above, it is an object of the present invention to provide a flexible tube for an endoscope which has an excellent antibacterial property.

In order to achieve the above object, the present invention is directed to a flexible tube for an endoscope, comprising:
  a flexible elongated structural body; and
  an outer cover provided over the elongated structural body, the outer cover having an outer peripheral part, and at least the outer peripheral part of the outer cover being made of a material which contains elastic resin and plant extract having an antibacterial property.

In this flexible tube, the plant extract and the resin that constitutes the outer cover are inert with respect to each other. Therefore, according to the present invention described above, it is possible to provide a flexible tube for an endoscope that can not only exhibit excellent antibacterial property against bacteria and the like, but also sustain the antibacterial property over a long period of time.

In the present invention, it is preferred that the outer cover includes an inner layer and an outer layer provided around the inner layer, in which the outer layer forms the outer peripheral part of the outer cover.

Further, in the present invention, it is also preferred that the content of the plant extract in the material for the outer cover is 0.1 to 30% by weight.

Furthermore, in the present invention, it is also preferred that the resin is at least one selected from the group consisting of polyvinyl chloride, polyurethane elastomer, polyester elastomer, polyolefin elastomer, polyamide elastomer, polystyrene elastomer, fluorine-based elastomer, and fluororubber.

Moreover, in the present invention, it is also preferred that the plant extract is obtained from at least one plant selected from the group consisting of plants belonging to the order Ranunculales. In this case, it is preferred that the plants belong to Nymphaeaceae and Ranunculaceae of the order Ranunculales.

Another aspect of the present invention is directed to a flexible tube for an endoscope, comprising:
  a flexible elongated structural body;
  an outer cover provided over the elongated structural body, the outer cover having an outer periphery and being made of a material which contains elastic resin; and
  a covering layer provided on the outer periphery of the outer cover, the covering layer being made of a material which contains plant extract having an antibacterial property.

In the present invention, it is preferred that the covering layer has a thickness of 0.01 to 0.25 mm.

Further, in the present invention, it is also preferred that the content of the plant extract in the material for the covering layer is 0.1 to 30% by weight.

These and other objects, structures and advantages of the present invention will be apparent more clearly from the following description of the invention based on the examples.

BRIEF DESCRIPTION OF THE DRAWINGS

FIG. 3 is a partial cross-sectional view which shows a second embodiment of the flexible tube for an endoscope according to the present invention.

DETAILED DESCRIPTION OF THE PREFERRED EMBODIMENTS

Hereinafter, a flexible tube for an endoscope according to the present invention will be described with reference to the appended drawings.

Figure 1:
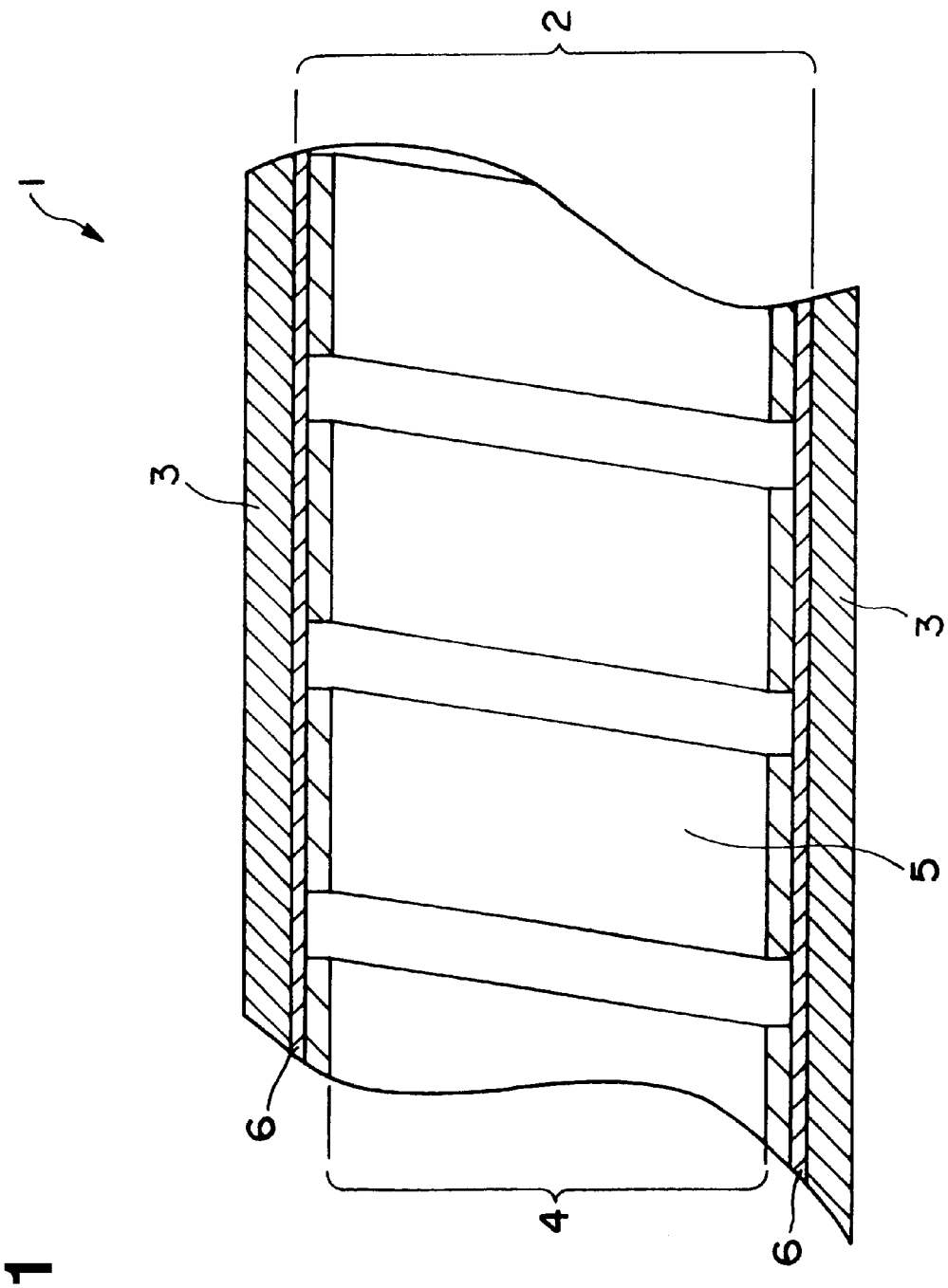
FIG. 1 is a partial cross-sectional view which shows a first embodiment of a flexible tube for an endoscope according to the present invention.

FIG. 1 is a partial cross-sectional view which shows a first embodiment of the flexible tube for an endoscope according to the present invention.

The flexible tube 1 is used in an insertion section of an endoscope which is designed to be inserted into a body cavity of a living body. As shown in FIG. 1, this flexible tube 1 is composed of a flexible elongated structural body 2 and an outer cover 3 which covers the outer periphery of the structural body 2. Further, inside the flexible tube 1, there is formed a hollow space 4 through which internal elements (such as optical fibers, cables, operation wires, tubular elements, and the like which are not shown in the drawings) can be passed.

The structural body 2 of the flexible tube 1 acts as a reinforcing member for reinforcing the flexible tube 1, and also acts as a protecting member for protecting the internal elements described above. This structural body 2 is constructed from a coil 5 and a reticular tube 6 which covers the outer periphery of the coil 5, so that the structural body 2 is formed into an elongated tubular shape. By constructing the structural body 2 using the coil 5 and the reticular tube 6, it becomes possible to give the flexible tube 1 torque transmission ability, tracking ability to a body cavity (i.e., bendability), and sufficient mechanical strength.

The coil 5 is formed from a flat metal band. Specifically, this coil 5 is formed by winding the metal band into a spiral form so as to have a uniform diameter and to provide a predetermined space between the adjacent windings. Preferred examples of materials which may be used for the metal band include stainless steel, copper alloys, and the like.

In this invention, a thickness of the band forming the coil 5 (that is, a wall thickness of the coil 5) is not limited to a specific value. Normally, it is preferable that the coil 5 is formed from a band that has a thickness in the range of approximately 0.10–0.5 mm, and more preferably in the range of approximately 0.12–0.4 mm. In the case where the coil 5 is formed from a band whose thickness is smaller than the lower limit of the range described above, there is a possibility that the structural body cannot sufficiently exhibit torque transmission ability and tracking ability to a body cavity (i.e., bendability). On the other hand, in the case where the coil 5 is formed from a band whose thickness is larger than the upper limit of the range described above, an outer diameter of the flexible tube 1 increases, and this is disadvantageous in reducing the diameter of the flexible tube.

The reticular tube 6 can be formed from fine metal wires woven together or from fine metal wires and nonmetal fibers woven together. Preferred examples of materials which may be used for the fine metal wires include stainless steel, copper alloys and the like. Further, preferred examples of materials which may be used for the nonmetal fibers include synthetic resin such as polyester, polyamide, polyvinyl chloride and the like.

In this invention, a thickness of the wires forming the reticular tube 6 (that is, a wall thickness of the reticular tube 6) is not limited to a specific value. Normally, it is preferable that the reticular tube 6 has a wall thickness in the range of approximately 0.03–0.22 mm, and more preferably in the range of approximately 0.035–0.20 mm. In the case where the reticular tube 6 has a wall thickness smaller than the lower limit of the range described above, there is a possibility that the structural body 2 cannot sufficiently exhibit torque transmission ability and tracking ability to a body cavity (i.e., bendability). On the other hand, in the case where the reticular tube 6 has a wall thickness larger than the upper limit of the range described above, an outer diameter of the flexible tube 1 increases, and this is disadvantageous in reducing the diameter of the flexible tube.

As shown in FIG. 1, the outer cover 3 of the flexible tube 1 covers the outer periphery of the structural body 2. By providing such an outer cover, it becomes possible to improve the ease of the inserting operation (that is, its flexibility) and to reduce the burden on patients. Further, it also becomes possible to prevent body fluids and the like from entering the inside of the endoscope (in particular, inside of the insertion section of the endoscope).

In this embodiment, a material used for producing the outer cover 3 (hereinafter referred to as "outer cover material") includes elastic resins and plant extracts having an antibacterial property.

Examples of such elastic resin include polyvinyl chlorides; polyolefins (such as polyethylene, polypropylene, ethylene-vinyl acetate copolymer, and the like); polyamides; polyesters (such as polyethylene terephthalate (PET), polybutylene terephthalate (PBT), and the like); polyurethanes; polystyrene-based resins; fluorine-based resins (such as polytetrafluoroethylene, ethylene-tetrafluoroethylene copolymer, and the like); polyimides; various elastomers (such as polyurethane elastomer, polyester elastomer, polyolefin elastomer, polyamide elastomer, polystyrene elastomer, fluorine-based elastomer, silicone rubber, fluororubber, latex rubber, and the like); and the like. These can be used alone or as mixtures of two or more thereof. Among the above, a resin containing at least one of polyvinyl chloride, polyurethane elastomer, polyester elastomer, polyolefin elastomer, polyamide elastomer, polystyrene elastomer, fluorine-based elastomer and fluororubber is preferably used in this invention.

Such a resin has sufficient elasticity, and hence the outer cover 3 can obtain good flexibility when the resin is used as a main component for the outer cover material.

In the case where polyvinyl chloride is used in this invention, the polyvinyl chloride may be prepared through a polymerization process such as bulk polymerization, suspension polymerization, emulsion polymerization, and the like, which is carried out by irradiating light, a-ray or the like, or using free radical polymerization catalyst such as peroxide and the like. In the polymerization process, cyclohexanone, tetrahydrofuran, nitrobenzene, or the like can be used as a solvent for causing the reaction. In the case of carrying out the polymerization process as described above, it is preferable that a processing temperature is about 150 to 170° C.

In this invention, it is preferable to add plasticizer such as di(2-ethylhexyl) phthalate to the polyvinyl chloride in order to improve flexibility of the flexible tube. Such a polyvinyl chloride preferably has a weight average molecular weight of about 25,000 to 30,000.

As for polyurethane elastomer to be used in this invention, for example, copolymers having hard segments and soft segments (such as random copolymers, block copolymers and the like) can be used.

Examples of the hard segments for the polyurethane elastomer include polymers which contain diisocyanate and short chain glycol, polymers which contain short chain glycol as a main component thereof, and the like. In this connection, examples of the diisocyanate include 4,4'-diphenylmethane diisocyanate (MDI), 2,4'-toluene diisocyanate (TDI), 2, 6-toluene diisocyanate (TDI), 1, 6-hexamethylene diisocyanate (HDI), 3,3'-dimethyldiphenyl-4,4'-diisocyanate (TODI), 1,5'-naphthalene diisocyanate (NDI), and the like. Among these substances, 4,4'-diphenylmethane diisocyanate (MDI) should preferably be used in this invention. Further, examples of the short chain glycol include ethylene glycol (EO), 1,3-propylene glycol (PG), 1,3-butylene glycol, 1,4-butylene glycol, 1,6-hexyl glycol, 1,4-dimethylolbenzene, bisphenol A, bisphenol A/EO, and the like. Among these substances, 1, 4-butylene glycol should preferably be used in this invention.

Examples of the soft segments for the polyurethane elastomer include polymers which contain diisocyanate and long chain glycol, polymers which contain long chain glycol as a main component thereof, and the like. In this connection, examples of the diisocyanate include substances which are the same as those mentioned with reference to the hard segments, and among those substances 4,4'-diphenylmethane diisocyanate (MDI) should preferably be used in this invention. Further, examples of the long chain glycol include polytetra methylene ether glycol (PTMG), poly(oxypropylene) glycol, poly(ethylene adipate)glycol, poly(butylene-1,4-adipate)glycol, poly(ethylene-1,4-adipate)glycol, poly(hexanediol-1,6-carbonate)glycol, polycaprolactone glycol, poly(diethylene glycol adipate)glycol, (hexanediol-1,6-carbonate)glycol, and the like. Among these substances, polytetra methylene ether glycol (PTMG) should preferably be used in this invention.

As for polyester elastomer to be used in this invention, for example, copolymers having hard segments and soft segments (such as random copolymers, block copolymers and the like) can be used. In this regard, the polyester elastomer is classified into a polyester-polyether type polyester elastomer, a polyester-polyester type polyester elastomer, and a liquid crystal type polyester elastomer.

Examples of the hard segments for the polyester-polyether type polyester elastomer include polybutylene terephthalate (PBT), polyethylene terephthalate (PET), and the like.

Examples of the soft segments for the polyester-polyether type polyester elastomer include polytetra methylene ether glycol (PTMG), poly(1, 2-propylene oxide)glycol, poly(ethylene oxide)glycol, and the like.

Examples of the hard segments for the polyester-polyester type polyester elastomer include polybutylene terephthalate (PBT), and the like.

Examples of the soft segments for the polyester-polyester type polyester elastomer include polycaprolactone, and the like.

Examples of the hard segments for the liquid crystal type polyester elastomer include dihydroxy paraquarterphenyl (DHQ), and the like.

Example of the soft segments for the liquid crystal type polyester elastomer include aromatic-based polyester (e.g., polyethylene terephthalate), and the like.

Among these substances described above, the polybutylene terephthalate should preferably be used for the hard segments of the polyester elastomer. Further, the polytetra methylene ether glycol should preferably be used for the soft segments of the polyester elastomer.

As for polyolefin elastomer to be used in this invention, for example, copolymers having hard segments and soft segments (such as random copolymers, block copolymers and the like) can be used.

Examples of the hard segments for the polyolefin elastomer include polypropylene (PP), polyethylene (PE), polystyrene (PS), styrene-butadiene-acrylonitrile (ABS), styrene-acrylonitrile (SAN), polycarbonate (PC), and the like. Among these substances, polyethylene (PE) should preferably be used in this invention.

Examples of the soft segments for the polyolefin elastomer include ethylene-propylene-diene copolymer (EPDM), ethylene-propylene copolymer (EPM), natural rubber (NR), butadiene rubber (BR), ethylene-vinyl acetate (EVA), chloroprene rubber (CR), acrylonitrile-butadiene rubber (NBR), and the like. Among these substances, ethylene-propylene-diene copolymer (EPDM) should preferably be used in this invention.

As for polyamide elastomer to be used in this invention, for example, copolymers having hard segments and soft segments (such as random copolymers, block copolymers and the like) can be used.

Examples of the hard segments for the polyamide elastomer include nylon 6, nylon 66, nylon 610, nylon 11, nylon 12, and the like. Among these substances, nylon 66 should preferably be used in this invention.

Examples of the soft segments for the polyamide elastomer include polytetra methylene ether glycol (PTMG), poly(oxypropylene)glycol, poly(ethylene adipate)glycol, poly(butylene-1,4-adipate)glycol, and the like. Among these substances, polytetra methylene ether glycol (PTMG) should preferably be used in this invention.

As for polystyrene elastomer to be used in this invention, for example, copolymers having hard segments and soft segments (such as random copolymers, block copolymers and the like) can be used.

Examples of the hard segments for the polystyrene elastomer include polystyrene and the like.

Examples of the soft segments for the polystyrene elastomer include polydiene (such as polybutadiene, polyisoprene and the like) and the like. Among these substances, polybutadiene should preferably be used in this invention.

As for fluorine-based elastomer to be used in this invention, for example, copolymers having hard segments and soft segments (such as random copolymers, block copolymers and the like) can be used.

Examples of the hard segments for the fluorine-based elastomer include fluororesin (such as tetrafluoroethylene-ethylene copolymer, polyvinylidene fluoride, and the like) and the like. Among these substances, tetrafluoroethylene-ethylene copolymer should preferably be used in this invention.

Examples of the soft segments for the fluorine-based elastomer include fluororubber (such as vinylidene fluoride-hexafluoropropylene-tetrafluoroethylene terpolymer and the like) and the like. Among these substances, polybutadiene should preferably be used in this invention.

Examples of fluororubber to be used in this invention include vinylidene fluoride-based fluororubber, tetrafluoroethylene/propylene-based robber, perfluoro fluororubber, fluorosilicone rubber, fluorophosphazene rubber, and the like. Among these substances, vinylidene fluoride-based fluororubber is preferably used in this invention.

In this invention, it is preferred that the plant extracts have an antibacterial property against bacteria, virus and the like. In this connection, it is to be noted that the meaning given by the term "antibacterial property" used herein includes the property of inhibiting propagation of bacteria, as well as the property of killing bacteria to decrease the number of bacteria alive.

The plant to be used in the present invention is not particularly limited so long as it contains antibacterial substances. Examples of the plant to be used in this invention include plants belonging to Nymphaeaceae, Ranunculaceae, Menispermaceae, and Berberidaceae among those belonging to the order Ranunculales (that is, belonging to the order Ranunculales, the subclass Choripetalae, the class Dioctyledoneae, the subphylum Angiosperm of the phylum Spermatophyta). These may be used alone or as mixtures of two or more thereof. Among the above, plants belonging to Nymphaeaceae and Ranunculaceae are preferably used in this invention.

Examples of plants belonging to such families include *Nelumbo nucifera* Gaertner, *Coptis japonica* Makino, plants congeneric to *Coptis japonica* Makino, and *Hydrastis canadensis* L. Among these plants, *Nelumbo nucifera* Gaertner, *Coptis japonica* Makino, and plants congeneric to *Coptis japonica* Makino are preferably used in this invention. Each of these plants contains, as its main component, an antibacterial substance having a high antibacterial property. For this reason, when a plant extract obtained from these plants is added to an outer cover material, it is possible to obtain the outer cover 3 having an excellent antibacterial property.

Now, it is to be noted that the antibacterial property against bacteria and the like will not be impaired, even when such a plant extract is mixed with the above-mentioned resin. This is because the plant extract is inert with respect to the resin. For this reason, the antibacterial property of the outer cover 3 of the flexible tube 1 is sustained over a long period of time.

In this invention, site of the plant used for obtaining the plant extract is not particularly limited, and such a site is appropriately selected depending on a kind of plant to be used. For example, one site selected from the whole plant, rhizome, root, subterranean stem, leaf, fruit, seed, skin, stem, fat and flower may be used to obtain the plant extract, or a combination of two sites or more may be used. Further, such a plant may directly be used as it is, or may be used after drying. In the case of using seeds, such seeds maybe used after roasting.

In this invention, an extraction method for obtaining plant extracts is not particularly limited. Examples of such an extraction method include a squeeze method, a steam distillation method, a method using various solvents, and the like. Among these methods, the method using a solvent is preferably used as the extraction method in this invention. In this case, a solvent to be used for extraction is not particularly limited. Examples of such a solvent include water; a salt solution prepared by adding an inorganic salt to water; alcohols such as ethanol and methanol; an aqueous solution of such alcohols; organic solvents such as petroleum ether, ethyl acetate, acetone, and the like. Among these solvents, water and ethanol aqueous solution are preferably used in this invention.

Temperature of the solvent in the extraction process for obtaining plant extracts is not particularly limited. In the case where water is used as the solvent, the temperature is preferably 4 to 100° C., more preferably 15 to 70° C. However, in the case where materials other than water are used as the solvent, the solvent temperature is not limited to the above temperature.

The plant extract thus obtained can be used, for example, in the form of a concentrated liquid obtained by concentrating an extracted solution of the plant extract, or in the form of a dried extract obtained by drying the concentrated liquid. In this connection, a method for concentrating the extracted solution is not particularly limited. Examples of such a concentration method include a method of heating a solvent to its boiling point or higher, a method of heating a solvent under a reduced pressure, and the like. Among these methods, the method of heating a solvent under a reduced pressure is preferable. The method of heating a solvent under a reduced pressure can easily remove a solvent at a relatively low temperature. For this reason, this method is particularly advantageous in removing a large amount of solvent.

In this invention, a content of the plant extract in the outer cover material is not particularly limited. The content of the plant extract in the outer cover material is preferably 0.1 to 30% by weight, more preferably 0.5 to 25% by weight. In the case where the content of the plant extract in the outer cover material is too small, there is a possibility that the outer cover 3 cannot sufficiently exhibit antibacterial property against bacteria and the like depending on the kind of bacteria. On the other hand, in the case where the content of the plant extract in the outer cover material is too large, there is a possibility that the plant extract impairs physical characteristics of the outer cover material, such as flexibility.

If desired and necessary, the outer cover material may optionally contain additives. Examples of the additives include inorganic fillers, pigments, various stabilizers (such as antioxidants, light stabilizers, antistatic agents, antiblocking agents, lubricants, and the like), and X-ray contrast medium.

The flexible tube 1 of an endoscope according to the present invention is produced, for example, as follows.

First, an outer periphery of a coil 5 is covered with a reticular tube 6 to produce a structural body 2. Next, an outer cover material is melted or softened with an extrusion molding machine to uniformly mix the material. In this mixing process, temperature of the outer cover material is not particularly limited. The temperature is preferably about 160 to 220° C., more preferably about 180 to 210° C. In the case where the outer cover material temperature in the mixing process is too low, there is a possibility that the outer cover material is not sufficiently mixed. On the other hand, in the case where the outer cover material temperature in the mixing process is too high, there is a possibility that plant extract contained in the outer cover material changes its quality.

Next, the outer cover material is extruded in such a manner that the structural body 2 is continuously covered with the outer cover 3 having an uniform thickness (that is, in such a manner that an elongated tubular body made from the outer cover material is provided over the outer periphery of the structural body 2). In this connection, a temperature of the outer cover 3 in the extrusion molding may be set to substantially the same temperature as that of the outer cover material in the mixing process mentioned above.

Thus, the flexible tube 1 for an endoscope is obtained.

Thickness of the outer cover 3 is not particularly limited so long as it can protect the structural body 2 and the above-mentioned internal elements inserted therein from a body fluid and does not deteriorate the bendability of the flexible tube 1. In general, the thickness is preferably about 0.05 to 0.95 mm, more preferably about 0.1 to 0.85 mm.

Now, it should be noted that the method of producing a flexible tube for an endoscope of the present invention is not limited to the embodiment described above. For example, a flexible tube for an endoscope may be produced in the following manner. Namely, first the outer cover material is formed into an elongated tubular body to obtain an outer cover 3 for covering the outer periphery of a structural body 2, and then the structural body 2 is inserted into thus obtained outer cover 3 having an elongated tubular shape. Next, the outer cover 3 in which the structural body 2 has been inserted is subjected to a bonding treatment such as heating to produce a flexible tube for an endoscope.

Figure 2:
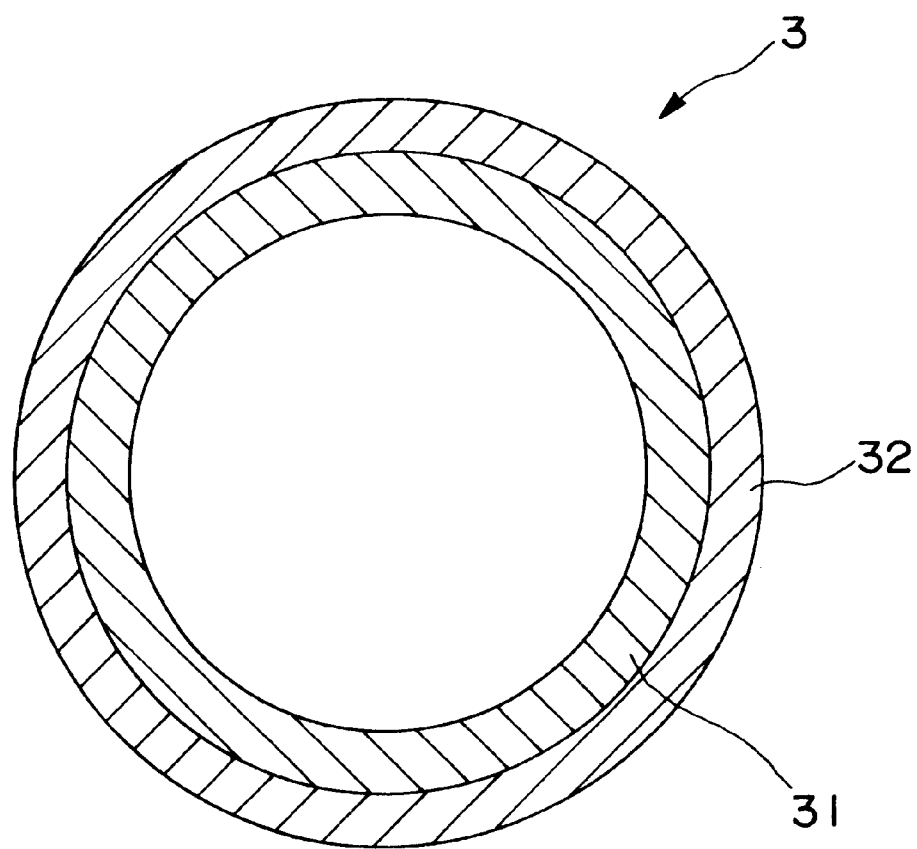
FIG. 2 is a cross sectional view which shows an outer cover provided on the outer periphery of a structural body of the flexible tube in FIG. 1.

The outer cover 3 is not limited to one constituted of a single layer as shown in FIG. 1, and may be constituted of a plurality of layers. For example, as shown in FIG. 2, the outer cover 3 may be constituted of two layers of an inner layer 31 and an outer layer 32 provided on the outer periphery of the inner layer 31. In this case, it is preferable that the outer layer 32 is formed of an outer cover material containing a plant extract, and the inner layer 31 is formed of an outer cover material containing no plant extract. In such a case, the resins as described above with reference to the first embodiment may be used to form the inner and outer layers 31 and 32.

Thickness of the outer layer 32 is preferably about 0.01 to 0.25 mm, more preferably about 0.015 to 0.20 mm. In the case where the thickness of the outer layer 32 is too small, there is a possibility that it cannot sufficiently exhibit the antibacterial property against bacteria and the like. On the other hand, in the case where the thickness of the outer layer 32 is too large, an outer diameter of the flexible tube 1 of the insertion section increases, and this is disadvantageous in reducing the diameter of the flexible tube.

The outer cover material for the inner layer 31 and the outer cover material for the outer layer 32 may be molded into an integral body by utilizing, for example, a double extrusion molding method (two-color extrusion molding method). Alternatively, the outer cover material for the inner layer 31 and the outer cover material for the outer layer 32 may also be separately molded into a hollow tubular body. In the latter case, after covering the tubular body constituting the inner layer 31 with the tubular body constituting the outer layer 32, a bonding treatment such as heating may be carried out to these tubular bodies to bond them together.

Next, a second embodiment of the flexible tube for an endoscope according to the present invention will be described with reference to FIG. 3. In this connection, the following description is given mainly with regard to differences from the above-mentioned first embodiment, and with regard to the common elements the explanation is omitted.

FIG. 3 is a partial cross-sectional view which shows the second embodiment of the flexible tube for the endoscope according to the present invention.

As shown in FIG. 3, the second embodiment of the flexible tube 1 according to the present invention includes a structural body 2, an outer cover 3 produced onto the outer periphery the structural body 2, and a covering layer 7 containing a plant extract, formed on the outer periphery of the outer cover 3.

In this embodiment, the outer cover 3 is formed from the same material as in the first embodiment, except for not containing the plant extract as described above.

The covering layer 7 is preferably formed using a material containing the above-mentioned plant extract and a polymer. The polymer is used in order to retain the plant extract in the covering layer 7. In this invention, the polymer to be used is not particularly limited. Preferred examples of such a polymer include polyvinyl alcohol (PVA), cellulose derivatives (such as methyl cellulose and ethyl cellulose), and the like. Among these substances, polyvinyl alcohol is preferably used in this invention. Such a polymer has high compatibility with the resin constituting the outer cover. For this reason, the covering layer 7 has improved adhesiveness to the outer cover 3.

Thickness of the covering layer 7 is not particularly limited. The thickness is preferably about 0.01 to 0.25 mm, more preferably 0.015 to 0.2 mm. In the case where the thickness of the covering layer 7 is too small, there is a possibility that it does not exhibit a sufficient antibacterial property against bacteria and the like. On the other hand, in the case where the thickness of the covering layer 7 is too large, an outer diameter of the flexible tube 1 of the insertion section increases, and this is disadvantageous in reducing the diameter of the flexible tube.

A content of the plant extract in the covering layer 7 is not particularly limited. The content of the plant extract in the covering layer 7 is preferably 0.1 to 30% by weight, more preferably 0.5 to 25% by weight. In the case where the content of the plant extract in the covering layer 7 is too small, there is a possibility that it cannot exhibit a sufficient antibacterial property against bacteria and the like depending on the type of the bacteria and the like. On the other hand, in the case where the content of the plant extract in the covering layer 7 is set above the upper limit, further improvement in the antibacterial property is not obtained.

Such a covering layer can be formed on the outer periphery of the outer cover 3 by, for example, the following manner.

If desired and necessary, fine unevenness may be formed on the surface of the outer cover 3. Examples of a method of forming such fine unevenness include mat finish treatment, chemical treatment (e.g., acid treatment such as hydrochloric acid treatment), shot blast, and sand blast. Further, such fine unevenness can also be formed by properly selecting the shape of an extrusion nozzle of the extrusion molding machine. By forming such fine unevenness on the outer cover 3, it becomes possible to improve adhesiveness of the covering layer 7 to the outer cover 3.

Next, the surface of the outer cover 3 is coated (or impregnated) with, for example, an organic solvent in which the plant extract and polymer are dissolved, which is then dried. This effectively forms the covering layer 7 on the outer periphery of the outer cover 3. As for the organic solvent, it is preferable to use an organic solvent that can appropriately dissolve or swell the resin constituting the outer cover. Examples of such an organic solvent preferably used include tetrahydrofuran, dimethylformamide, and the like. Use of such an organic solvent improves adhesiveness of the covering layer 7 to the outer cover 3.

The flexible tube for an endoscope according to the present invention was described above with reference to the embodiments illustrated in the accompanying drawings, but this invention is not limited to these embodiments. For example, the flexible tube for an endoscope according to the present invention can been applied to other site of the endoscope such as a flexible tube for a light guide connected to a light source device.

EXAMPLES

Next, specific examples of the present invention will be described below.

EXAMPLE 1

<1-1>Preparation of Plant Extract (In the Form of a Concentrated Liquid)

5 g of dried leaves of *Nelumbo nucifera* Gaertner and 5 g of dried rhizome of *Coptis japonica* Makino were minced. The minced plants were dipped in 500 ml of water held at 25° C., and then stirred for 1 hour. Next, the resulting liquid was filtered with a filter paper, and the filtrate was concentrated with a vacuum evaporator under a condition heated at 60° C. In this way, 1.2 g of a plant extract in the form of a concentrated liquid was obtained.

<1-2>Production of Flexible Tube for Endoscope

A flexible tube for an endoscope having an outer cover of a single layer as shown in FIG. 1 was produced as follows.

The following resins (1)–(8) were selectively used for preparing the outer cover.

(1) Polyvinyl Chloride

Polyvinyl chloride to which emulsion polymerization was carried out and then di(2-ethylhexyl) phthalate was added to plasticize it. (The polyvinyl chloride had a weight average molecular weight of 28,000.)

(2) Polyurethane Elastomer

Block copolymer having hard segments of 1,4-butylene glycol and soft segments of polytetramethylene ether glycol.

(3) Polyester Elastomer

Block copolymer having hard segments of polybutylene terephthalate and soft segments of polytetramethylene ether glycol.

(4) Polyolefin Elastomer

Block copolymer having hard segments of polyethylene and soft segments of ethylene-propylene-diene copolymer.

(5) Polyamide Elastomer

Block copolymer having hard segments of nylon 66 and soft segments of polytetramethylene ether glycol.

(6) Polystyrene Elastomer

Block copolymer having hard segments of polystyrene and soft segments of polybutadiene.

(7) Fluorine-Based Elastomer

Block copolymer having hard segments of tetrafluoroethylene-ethylene copolymer and soft segments of vinylidene fluoride-hexafluoropropylene-tetrafluoroethylene terpolymer.

(8) Fluororubber

Vinylidene fluoride type fluororubber.

First, a structural body was produced from a stainless steel coil and a reticular tube formed by weaving together stainless steel metal wires and non-metal polyester fibers.

Next, the plant extract (in the form of a concentrated liquid) and a resin used for producing an outer cover were introduced into an extrusion molding machine, and then mixed at 180° C.

Next, an outer cover material in the extrusion molding machine was heated at 180° C., and then the outer cover material was molded into an elongated tubular body, so that an outer periphery of the structural body was covered with the tubular body (outer cover) having a thickness of 0.5 mm. In this way, a flexible tube for an endoscope having an inner diameter of 7 mm, and outer diameter of 9 mm and a length of 1.5 m was produced.

In accordance with the method mentioned above, 12 types of flexible tubes (samples of this invention) were manufactured, which were different from each other in a kind of resin(s) forming the outer cover. Further, another 12 types of flexible tubes (samples of comparative Examples) were also manufactured using the same resin(s) as in the samples of this invention. In this connection, it should be noted that the samples of comparative Examples (sample No. 13–24) were manufactured without using any plant extract for the purpose of comparison with the samples of this invention (sample No. 1–12).

A kind of the resin(s) used in each sample of this Example, a compounding ratio of the resins, and a content of the plant extract (in the form of a concentrated liquid) added to the respective outer cover material are shown in Table 1.

EXAMPLE 2

<2-1>Preparation of Plant Extract (Dried Extract)

First, a concentrated liquid was prepared in accordance with the same manner as in Example 1.

Next, 1.2 g of the concentrated liquid thus obtained was dried at 70° C. for 24 hours to obtain 0.8 g of a dried plant extract.

<2-2>Production of Flexible Tube for Endoscope

A flexible tube for an endoscope having an outer cover constituted of two layers of an inner layer and an outer layer as shown in FIG. 2 was produced as follows.

In this Example, ethylene-vinyl acetate copolymer was used as a resin for the inner layer of the outer cover. Further, the same resin as in Example 1 was used as a resin for the outer layer of the outer cover.

First, a structural body was produced from a stainless steel coil and a reticular tube formed by weaving together stainless steel metal wires and non-metal polyester fibers.

Next, the dried plant extract and the resin for producing the outer layer of the outer cover were introduced into the extrusion molding machine, and then mixed at 180° C. Further, the resin for producing the inner layer of the outer cover was introduced into the extrusion molding machine, and melted at 180° C.

Next, an outer cover material for both the inner and outer layers in the extrusion molding machine was heated at 180° C., and then the outer cover material was molded into an elongated tubular body utilizing a double extrusion molding method (two-color extrusion molding method) so as to have across section as shown in FIG. 2. In this extrusion process, the outer cover material was extruded so that an outer periphery of the structural body was covered with the tubular body (outer cover) having a thickness of 0.5 mm (inner layer: 0.3 mm, outer layer: 0.2 mm). In this way, a flexible tube for an endoscope having an inner diameter of 7 mm, and outer diameter of 9 mm and a length of 1.5 m was produced.

In accordance with the method mentioned above, 12 types of flexible tubes (samples of this invention) were manufactured, which were different from each other in a kind of resin(s) forming the outer layer of the outer cover. Further, another 12 types of flexible tubes (samples of comparative Examples) were also manufactured using the same resin(s) as in the samples of this invention. In this connection, it should be noted that the samples of comparative Examples (sample No. 37–48) were manufactured without using any plant extract for the purpose of comparison with the samples of this invention (sample No. 25–36).

A kind of the resin(s) used in each sample of this Example, a compounding ratio of the resins, and a content of the dried plant extract added to the material for the respective outer layer are shown in Table 2.

EXAMPLE 3

<3-1>Preparation of Plant Extract (in the form of concentrated liquid)

A concentrated liquid was prepared in the same manner as in Example 1.

<3-2>Production of Flexible Tube for Endoscope

A flexible tube (as shown in FIG. 3) for an endoscope having a covering layer formed on an outer periphery of an outer cover was produced as follows. In this Example, the same resin as the one used in Example 1 was used as a resin for producing the outer cover.

First, a structural body was produced from a stainless steel coil and a reticular tube formed by weaving together stainless steel metal wires and non-metal polyester fibers.

Next, a resin for producing an outer cover was introduced into the extrusion molding machine, and then mixed at 180° C.

Next, an outer cover material in the extrusion molding machine was heated at 180° C., and then the outer cover material was molded into an elongated tubular body, so that an outer periphery of the structural body was covered with the tubular body (outer cover) having a thickness of 0.5 mm. In this way, a flexible tube for an endoscope having an inner diameter of 7 mm, and an outer diameter of 9 mm and a length of 1.5 m was produced.

Next, a mat finish treatment was carried out to the outer cover of the produced flexible tube using hydrochloric acid to roughen its outer surface.

Next, a dimethylformamide solution in which the plant extract (in the form of a concentrated liquid) and polyvinyl alcohol were dissolved was applied to the outer surface of the outer cover, and then dried at 170° C.

In this way, a covering layer as shown in FIG. 3 was formed on the outer periphery of the outer cover. Thickness (in the dried state) of the covering layer, and a content (in the dried state) of the plant extract in the covering layer are shown in Table 3.

In accordance with the method mentioned above, 12 types of flexible tubes (samples of this invention) were manufactured, which were different from each other in a kind of resin(s) forming the outer cover. Further, another 12 types of flexible tubes (samples of comparative Examples) were also manufactured using the same resin(s) as in the samples of this invention. In this connection, it should be noted that the samples of comparative Examples (sample No. 61–72) were manufactured without using any plant extract for the purpose of comparison with the samples of this invention (sample No. 49–60).

A kind of the resin(s) used in each sample of this Example, and a compounding ratio of the resins in each sample are shown in Table 3.

EXAMPLE 4

<4-1>Preparation of Plant Extract (Dried Extract)

A dried plant extract was prepared in the same manner as in Example 2.

<4-2>Production of Flexible Tube for Endoscope

A flexible tube for an endoscope having a covering layer formed on an outer periphery of an outer cover was produced as follows.

In this Example, the same resin as the one used in Example 1 was used as a resin for producing the outer cover.

A flexible tube for an endoscope having the covering layer formed on the outer periphery of the outer cover was produced in the same manner as in Example 3 except that a dried plant extract was used in place of a plant extract in the form of a concentrated liquid.

In this way, a covering layer as shown in FIG. 3 was formed on the outer periphery of the outer cover. Thickness (in the dried state) of the covering layer, and a content (in the dried state) of the plant extract in the covering layer are shown in Table 4.

In accordance with the method mentioned above, 12 types of flexible tubes (samples of this invention) were manufactured, which were different from each other in a kind of resin(s) forming the outer cover. Further, another 12 types of flexible tubes (samples of comparative Examples) were also manufactured using the same resin(s) as in the samples of this invention. In this connection, it should be noted that the samples of comparative Examples (sample No. 85–96) were manufactured without using any plant extract for the purpose of comparison with the samples of this invention (sample No. 73–84).

A kind of the resin(s) used in each sample of this Example, and a compounding ratio of the resins in each sample are shown in Table 4.

Evaluation

Fungus (such as bacteria) resistance test was conducted on each of the flexible tubes (sample Nos. 1 to 96 shown in Tables. 1–4) produced in Examples 1–4 by the test method according to JIS (Japanese Industrial Standards) Z2911 to evaluate an antibacterial property of the outer surface of each of the flexible tubes.

The test results were evaluated in accordance with the three rankings 1–3 given below.

1: Growth of fungus was not observed on the test sample.

2: Growth of fungus was observed on the test sample (growth area <⅓).

3: Growth of fungus was observed on the test sample (growth area >⅓).

The test results obtained are shown in the appended Tables 1–4.

The results in Tables 1 to 4 show that all of the flexible tubes according to the present invention (sample Nos. 1–12, 25–36, 49–60 and 73–84) exhibit excellent antibacterial property against bacteria and the like. Further, the results also show that the flexible tubes of the comparative examples (sample Nos. 13–24, 37–48, 61–72 and 85–96) are poor in the antibacterial property against bacteria and the like.

Further, the results in Tables 1 to 4 also show that all of the flexible tubes of the sample Nos. 1–12 and 25–36 exhibit excellent antibacterial property against bacteria and the like, despite the fact that the respective outer covers were produced through the high temperature condition. This means that even when the outer cover is provided on the structural body through the high temperature condition, the excellent antibacterial property of the plant extract in the flexible tube is maintained while changes in property and quality of the plant extract are suppressed.

As described above, the flexible tube for an endoscope according to the present invention exhibits excellent antibacterial property against bacteria and the like. Therefore, the flexible tube for an endoscope according to the present invention can reduce the number of live bacteria and the like on the surface thereof as much as possible.

Further, in the flexible tube for an endoscope according to the present invention, the plant extract and the resin that constitutes the outer cover are inert with respect to each other. Therefore, the antibacterial property against bacteria and the like of the flexible tube can be sustained over a long period of time.

Furthermore, the flexible tube for an endoscope according to the present invention can retain and exhibit the excellent antibacterial property against bacteria and the like even when it undergoes high temperature environment in manufacturing process, or during high temperature sterilization treatment.

Finally, it is to be understood that many changes and additions may be made to the embodiments described above without departing from the scope and spirit of the invention as defined in the appended claims.

Further, it is also to be understood that the present disclosure relates to subject matter contained in Japanese Patent Application No. 2000-013105 (filed on Jan. 21, 2000) which is expressly incorporated herein by reference in its entirety.

TABLE 1

(EXAMPLE 1)

| Sample No. | Resin(s) Forming Outer Cover | Content of Plant Extract* (percentage by weight) | Results of Fungus Resistance Test |
|---|---|---|---|
| | Samples of This Invention | | |
| 1 | Polyvinyl Chloride | 1 | 1 |
| 2 | Polyurethane Elastomer | 1 | 1 |
| 3 | Polyester Elastomer | 1 | 1 |
| 4 | Polyolefin Elastomer | 1 | 1 |
| 5 | Polyamide Elastomer | 1 | 1 |
| 6 | Polystyrene Elastomer | 1 | 1 |
| 7 | Fluorine-Based Elastomer | 1 | 1 |
| 8 | Fluororubber | 1 | 1 |
| 9 | Polyvinyl Chloride:Polyurethane Elastomer:Polyester Elastomer: Polyolefin Elastomer = 1:1:1:1 (parts by weight) | 1 | 1 |
| 10 | Polyvinyl Chloride:Polyamide Elastomer:Polystyrene Elastomer: Fluorine-Based Elastomer = 1:1:1:1 (parts by weight) | 1 | 1 |
| 11 | Polyurethane Elastomer:Polyester Elastomer:Polyolefin Elastomer: Fluororubber = 1:1:1:1 (parts by weight) | 1 | 1 |
| 12 | Polyvinyl Chloride:Polyamide Elastomer:Polystyrene Elastomer: Fluorine-Based Elastomer: Fluororubber = 1:1:1:1:1 (parts by weight) | 1 | 1 |

TABLE 1-continued

(EXAMPLE 1)

| Sample No. | Resin(s) Forming Outer Cover | Content of Plant Extract* (percentage by weight) | Results of Fungus Resistance Test |
|---|---|---|---|
| *Samples of Compar. Ex.* | | | |
| 13 | Polyvinyl Chloride | 0 | 3 |
| 14 | Polyurethane Elastomer | 0 | 3 |
| 15 | Polyester Elastomer | 0 | 3 |
| 16 | Polyolefin Elastomer | 0 | 3 |
| 17 | Polyamide Elastomer | 0 | 3 |
| 18 | Polystyrene Elastomer | 0 | 3 |
| 19 | Fluorine-Based Elastomer | 0 | 3 |
| 20 | Fluororubber | 0 | 3 |
| 21 | Polyvinyl Chloride:Polyurethane Elastomer:Polyester Elastomer:Polyolefin Elastomer = 1:1:1:1 (parts by weight) | 0 | 3 |
| 22 | Polyvinyl Chloride:Polyamide Elastomer:Polystyrene Elastomer:Fluorine-Based Elastomer = 1:1:1:1 (parts by weight) | 0 | 3 |
| 23 | Polyurethane Elastomer:Polyester Elastomer:Polyolefin Elastomer:Fluororubber = 1:1:1:1 (parts by weight) | 0 | 3 |
| 24 | Polyvinyl Chloride:Polyamide Elastomer:Polystyrene Elastomer:Fluorine-Based Elastomer:Fluororubber = 1:1:1:1:1 (parts by weight) | 0 | 3 |

*Content of Plant Extract: This indicates the content of the plant extract (in the form of a concentrated liquid) in the outer cover material.

TABLE 2

(EXAMPLE 2)

| Sample No. | Resin(s) Forming Outer Layer of Outer Cover | Content of Plant Extract* (percentage by weight) | Results of Fungus Resistance Test |
|---|---|---|---|
| *Samples of This Invention* | | | |
| 25 | Polyvinyl Chloride | 10 | 1 |
| 26 | Polyurethane Elastomer | 10 | 1 |
| 27 | Polyester Elastomer | 10 | 1 |
| 28 | Polyolefin Elastomer | 10 | 1 |
| 29 | Polyamide Elastomer | 10 | 1 |
| 30 | Polystyrene Elastomer | 10 | 1 |
| 31 | Fluorine-Based Elastomer | 10 | 1 |
| 32 | Fluororubber | 10 | 1 |
| 33 | Polyvinyl Chloride:Polyurethane Elastomer:Polyester Elastomer:Polyolefin Elastomer = 1:1:1:1 (parts by weight) | 10 | 1 |
| 34 | Polyvinyl Chloride:Polyamide Elastomer:Polystyrene Elastomer:Fluorine-Based Elastomer = 1:1:1:1 (parts by weight) | 10 | 1 |
| 35 | Polyurethane Elastomer:Polyester Elastomer:Polyolefin Elastomer:Fluororubber = 1:1:1:1 (parts by weight) | 10 | 1 |
| 36 | Polyvinyl Chloride:Polyamide Elastomer:Polystyrene Elastomer:Fluorine-Based Elastomer:Fluororubber = 1:1:1:1:1 (parts by weight) | 10 | 1 |

TABLE 2-continued

(EXAMPLE 2)

| Sample No. | Resin(s) Forming Outer Layer of Outer Cover | Content of Plant Extract* (percentage by weight) | Results of Fungus Resistance Test |
|---|---|---|---|
| *Samples of Compar. Ex.* | | | |
| 37 | Polyvinyl Chloride | 0 | 3 |
| 38 | Polyurethane Elastomer | 0 | 3 |
| 39 | Polyester Elastomer | 0 | 3 |
| 40 | Polyolefin Elastomer | 0 | 3 |
| 41 | Polyamide Elastomer | 0 | 3 |
| 42 | Polystyrene Elastomer | 0 | 3 |
| 43 | Fluorine-Based Elastomer | 0 | 3 |
| 44 | Fluororubber | 0 | 3 |
| 45 | Polyvinyl Chloride:Polyurethane Elastomer:Polyester Elastomer:Polyolefin Elastomer = 1:1:1:1 (parts by weight) | 0 | 3 |
| 46 | Polyvinyl Chloride:Polyamide Elastomer:Polystyrene Elastomer:Fluorine-Based Elastomer = 1:1:1:1 (parts by weight) | 0 | 3 |
| 47 | Polyurethane Elastomer:Polyester Elastomer:Polyolefin Elastomer:Fluororubber = 1:1:1:1 (parts by weight) | 0 | 3 |
| 48 | Polyvinyl Chloride:Polyamide Elastomer:Polystyrene Elastomer:Fluorine-Based Elastomer:Fluororubber = 1:1:1:1:1 (parts by weight) | 0 | 3 |

*Content of Plant Extract: This indicates the content of the dried plant extract in the outer cover material for the outer layer.

TABLE 3

(EXAMPLE 3)

| Sample No. | Resin(s) Forming Outer Cover | Thickness of Covering Layer (mm) | Content of Plant Extract* (percentage by weight) | Results of Fungus Resistance Test |
|---|---|---|---|---|
| *Samples of This Invention* | | | | |
| 49 | Polyvinyl Chloride | 0.1 | 20 | 1 |
| 50 | Polyurethane Elastomer | 0.1 | 20 | 1 |
| 51 | Polyester Elastomer | 0.1 | 20 | 1 |
| 52 | Polyolefin Elastomer | 0.1 | 20 | 1 |
| 53 | Polyamide Elastomer | 0.1 | 20 | 1 |
| 54 | Polystyrene Elastomer | 0.1 | 20 | 1 |
| 55 | Fluorine-Based Elastomer | 0.1 | 20 | 1 |
| 56 | Fluororubber | 0.1 | 20 | 1 |
| 57 | Polyvinyl Chloride:Polyurethane Elastomer:Polyester Elastomer:Polyolefin Elastomer = 1:1:1:1 (parts by weight) | | | |
| 58 | Polyvinyl Chloride:Polyamide Elastomer:Polystyrene Elastomer:Fluorine-Based Elastomer = 1:1:1:1 (parts by weight) | 0.1 | 20 | 1 |
| 59 | Polyurethane Elastomer:Polyester Elastomer:Polyolefin Elastomer:Fluororubber = 1:1:1:1 (parts by weight) | 0.1 | 20 | 1 |

TABLE 3-continued

(EXAMPLE 3)

| Sample No. | Resin(s) Forming Outer Cover | Thickness of Covering Layer (mm) | Content of Plant Extract* (percentage by weight) | Results of Fungus Resistance Test |
|---|---|---|---|---|
| 60 | Polyvinyl Chloride: Polyamide Elastomer: Polystyrene Elastomer: Fluorine-Based Elastomer:Fluororubber = 1:1:1:1:1 (parts by weight) | 0.1 | 20 | 1 |
| *Samples of Compar. Ex.* | | | | |
| 61 | Polyvinyl Chloride | 0.1 | 0 | 3 |
| 62 | Polyurethane Elastomer | 0.1 | 0 | 3 |
| 63 | Polyester Elastomer | 0.1 | 0 | 3 |
| 64 | Polyolefin Elastomer | 0.1 | 0 | 3 |
| 65 | Polyamide Elastomer | 0.1 | 0 | 3 |
| 66 | Polystyrene Elastomer | 0.1 | 0 | 3 |
| 67 | Fluorine-Based Elastomer | 0.1 | 0 | 3 |
| 68 | Fluororubber | 0.1 | 0 | 3 |
| 69 | Polyvinyl Chloride: Polyurethane Elastomer: Polyester Elastomer: Polyolefin Elastomer = 1:1:1:1 (parts by weight) | 0.1 | 0 | 3 |
| 70 | Polyvinyl Chloride: Polyamide Elastomer: Polystyrene Elastomer: Fluorine-Based Elastomer = 1:1:1:1 (parts by weight) | 0.1 | 0 | 3 |
| 71 | Polyurethane Elastomer: Polyester Elastomer: Polyolefin Elastomer: Fluororubber = 1:1:1:1 (parts by weight) | 0.1 | 0 | 3 |
| 72 | Polyvinyl Chloride: Polyamide Elastomer: Polystyrene Elastomer: Fluorine-Based Elastomer:Fluororubber = 1:1:1:1:1 (parts by weight) | 0.1 | 0 | 3 |

*Content of Plant Extract: This indicates the content of the plant extract (in the form of a concentrated liquid) in the material for the covering layer.

TABLE 4

(EXAMPLE 4)

| Sample No. | Resin(s) Forming Outer Cover | Thickness of Covering Layer (mm) | Content of Plant Extract* (percentage by weight) | Results of Fungus Resistance Test |
|---|---|---|---|---|
| *Samples of This Invention* | | | | |
| 73 | Polyvinyl Chloride | 0.02 | 15 | 1 |
| 74 | Polyurethane Elastomer | 0.02 | 15 | 1 |
| 75 | Polyester Elastomer | 0.02 | 15 | 1 |
| 76 | Polyolefin Elastomer | 0.02 | 15 | 1 |
| 77 | Polyamide Elastomer | 0.02 | 15 | 1 |
| 78 | Polystyrene Elastomer | 0.02 | 15 | 1 |
| 79 | Fluorine-Based Elastomer | 0.02 | 15 | 1 |
| 80 | Fluororubber | 0.02 | 15 | 1 |
| 81 | Polyvinyl Chloride: Polyurethane Elastomer: Polyester Elastomer: Polyolefin Elastomer = 1:1:1:1 (parts by weight) | 0.02 | 15 | 1 |
| 82 | Polyvinyl Chloride: Polyamide Elastomer: Polystyrene Elastomer: Fluorine-Based Elastomer = 1:1:1:1 (parts by weight) | 0.02 | 15 | 1 |
| 83 | Polyurethane Elastomer: Polyester Elastomer: Polyolefin Elastomer: Fluororubber = 1:1:1:1 (parts by weight) | 0.02 | 15 | 1 |
| 84 | Polyvinyl Chloride: Polyamide Elastomer: Polystyrene Elastomer: Fluorine-Based Elastomer:Fluororubber = 1:1:1:1:1 (parts by weight) | 0.02 | 15 | 1 |
| *Samples of Compar. Ex.* | | | | |
| 85 | Polyvinyl Chloride | 0.02 | 0 | 3 |
| 86 | Polyurethane Elastomer | 0.02 | 0 | 3 |
| 87 | Polyester Elastomer | 0.02 | 0 | 3 |
| 88 | Polyolefin Elastomer | 0.02 | 0 | 3 |
| 89 | Polyamide Elastomer | 0.02 | 0 | 3 |
| 90 | Polystyrene Elastomer | 0.02 | 0 | 3 |
| 91 | Fluorine-Based Elastomer | 0.02 | 0 | 3 |
| 92 | Fluororubber | 0.02 | 0 | 3 |
| 93 | Polyvinyl Chloride: Polyurethane Elastomer: Polyester Elastomer: Polyolefin Elastomer = 1:1:1:1 (parts by weight) | 0.02 | 0 | 3 |
| 94 | Polyvinyl Chloride: Polyamide Elastomer: Polystyrene Elastomer: Fluorine-Based Elastomer = 1:1:1:1 (parts by weight) | 0.02 | 0 | 3 |
| 95 | Polyurethane Elastomer: Polyester Elastomer: Polyolefin Elastomer: Fluororubber = 1:1:1:1 (parts by weight) | 0.02 | 0 | 3 |
| 96 | Polyvinyl Chloride: Polyamide Elastomer: Polystyrene Elastomer: Fluorine-Based Elastomer:Fluororubber = 1:1:1:1:1 (parts by weight) | 0.02 | 0 | 3 |

*Content of Plant Extract: This indicates the content of the dried plant extract in the material for the covering layer.

What is claimed is:

1. A flexible tube for an endoscope, comprising:
a flexible elongated structural body; and
an outer cover provided over the elongated structural body, the outer cover having an outer peripheral part, and at least the outer peripheral part of the outer cover being made of a material which contains elastic resin and plant extract obtained from at least *Nelumbo nucifera* Gaertner.

2. The flexible tube according to claim 1, wherein the plant extract is in a form of a concentrated liquid extracted from leaves of *Nelumbo nucifera* Gaertner.

3. The flexible tube according to claim 1, wherein the plant extract is in a form of a dried powder.

4. The flexible tube according to claim 3, wherein the dried powder is obtained by drying a concentrated liquid extracted from leaves of *Nelumbo nucifera* Gaertner.

5. A flexible tube for an endoscope, comprising:

a flexible elongated structural body;

an outer cover provided over the elongated structural body, the outer cover having an outer periphery and being made of a material which contains elastic resin; and a covering layer provided on the outer periphery of the outer cover, the covering layer being made of a material which contains plant extract obtained from at least *Nelumbo nucifera* Gaertner.

6. The flexible tube according to claim 5, wherein the plant extract is in a form of a concentrated liquid extracted from leaves of *Nelumbo nucifera* Gaertner.

7. The flexible tube according to claim 5, wherein the plant extract is in a form of a dried powder.

8. The flexible tube according to claim 7, wherein the dried powder is obtained by drying a concentrated liquid extracted from leaves of *Nelumbo nucifera* Gaertner.

* * * * *